United States Patent [19]

Arndt et al.

[11] 4,061,491
[45] Dec. 6, 1977

[54] METHOD OF CONTROLLING WEED GROWTH IN RICE FIELDS WITH TRI-N-BUTYL TIN IMIDAZOLE

[75] Inventors: Friedrich Arndt, Berlin; Hans Plum, Heessen, both of Germany

[73] Assignee: Schering Aktiengesellschaft, Berlin, Germany

[21] Appl. No.: 557,285

[22] Filed: Mar. 11, 1975

[30] Foreign Application Priority Data

Apr. 18, 1974   Germany .............................. 2419208

[51] Int. Cl.$^2$ ......................... A01N 9/22; A01N 9/00; C07F 7/22
[52] U.S. Cl. .................... 71/92; 260/270 Q; 260/299; 260/414; 260/429.7; 71/90; 71/94; 71/97
[58] Field of Search ...................... 260/299; 71/92, 97, 71/94

[56] References Cited

U.S. PATENT DOCUMENTS

| 3,031,483 | 4/1962 | Koopmans et al. ............... 260/429.7 |
| 3,222,158 | 12/1965 | Sowa .................................. 71/97 |
| 3,361,554 | 1/1968 | Weissenburger ....................... 71/97 |
| 3,499,086 | 3/1970 | Brueckner et al. ................. 71/97 X |
| 3,764,292 | 10/1973 | Deinet ................................ 71/97 |
| 3,789,057 | 1/1974 | Reifenburg et al. ............. 260/429.7 |

FOREIGN PATENT DOCUMENTS

| 1,386,350 | 1/1965 | France. |
| 64/11873 | 6/1964 | Japan. |
| 64/24358 | 10/1964 | Japan. |
| 69/16391 | 7/1969 | Japan. |
| 69/4413 | 2/1969 | Japan. |
| 301,027 | 9/1965 | Netherlands. |
| 6,701,062 | 7/1968 | Netherlands. |

OTHER PUBLICATIONS

Luijten et al., Chemical Abstracts, vol. 60, 6860c, (1964).
Luijten et al., Chemical Abstracts, vol. 57, 3466d, (1962).
Gruen et al., Chemical Abstracts, vol. 60, 13098d, (1964).
Foldesi et al., Chemical Abstracts, vol. 64, 3591h, (1966).
Skinner, Chemical Abstracts, vol. 78, 114,241n, (1973).

Primary Examiner—R. Gallagher
Assistant Examiner—Diana G. Rivers
Attorney, Agent, or Firm—Joseph F. Padlon

[57] ABSTRACT

Compounds having herbicidal and algicidal action are provided of the general formula

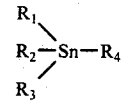

wherein $R_1$, $R_2$ and $R_3$ are identical or different alkyl radicals, and $R_4$ is an acid radical, or the radical of an acid compound or is

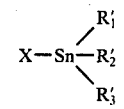

with $R_1'$, $R_2'$, and $R_3'$ having the meaning of $R_1$, $R_2$ or $R_3$ respectively, and wherein X represents oxygen or sulfur.

1 Claim, No Drawings

METHOD OF CONTROLLING WEED GROWTH IN RICE FIELDS WITH TRI-n-BUTYL TIN IMIDAZOLE

This invention relates to an agent having selective herbicidal and algicidal action; and in particular for the control of weeds and algae in cereal cultivation such as rice cultivation.

Weed control in rice, which is one of the cereal cultivations, is an important social problem since rice is one of the most important foods. There are presently agents which are used for weed control in rice. Such an agent is S-ethyl-N,N-hexamethylenethio carbamate, as disclosed in U.S. Pat. No. 3,198,786. This agent, however, is not always sufficiently compatible and shows no effective action against the algae occurring in rice cultivations.

With the above in view it is an object of the present invention therefore to make and provide a herbicidal agent which overcomes the disadvantages of heretofore known agents and is suitable particularly for the selective control of weeds and algae in cereal cultivation, including rice.

This is achieved according to the invention by an agent which is characterized by a content of at least one compound of the general formula

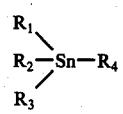  I in which $R_1$, $R_2$ and $R_3$ are identical or different alkyl radicals, which may also possibly be substituted, $R_4$ is an acid radical or the radical of an acid compound or the radical

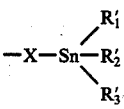  II with $R_1'$, $R_2'$ and $R_3'$ in the meaning of $R_1$, $R_2$ or $R_3$, respectively, and X is oxygen or sulfur.

Of the compounds of the stated general formula, there are those outstanding in which the radicals $R_1$, $R_2$ and $R_3$ are identical and represent, respectively, an alkyl radical with 1 to 8 carbon atoms or the benzyl radical, $R_4$ being the radical of the hydrohalic or pseudo hydrohalic acid, the radical of an oxygen-, sulfur-, or nitrogen-acid compound or the radical

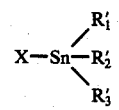  III with $R_1'$, $R_2'$ or $R_3'$ in the meaning of $R_1$, $R_2$ or $R_3$, and X being an oxygen or a sulfur atom. Surprisingly, the active substances to be used according to the invention are more compatible with cereal species, in particular rice, than the known S-ethyl-N,N-hexamethylenethio carbamate (common name molinate) and show moreover a better herbicidal effect than the latter.

The herbicidal action extends to many weed species, including grass, particularly millet species, as for example Echinochloa crus galli, which are effectively controlled. It should be stressed, however, that the active substances are suitable also for the control of Eleocharis acicularis, a very bothersome perennial weed widespread in rice cultivation, which cannot be controlled effectively with the known herbicide. The quantities to be used for selective weed control are about 2 to 5 kg active substance per hectare, but the quantity can in specific cases be reduced to 0.5 kg/ha or increased to 10 kg/ha.

The compounds to be used according to the invention can be employed either alone, in mixture with one another, or in mixture with other active substances. If desired, other plant protection or pest control agents, such as fungicides, nematocides or other agents can be added, according to the desired purpose. A fertilizer may also be added.

Expediently, the active substances of the invention are applied in the form of powders, scatters, granulates, solutions, emulsions or suspensions, with addition of liquid and/or solid vehicles or diluents and possibly of wetting, adhesive, emulsifying and/or dispersing aids.

Suitable liquid vehicles are, for example, water, aliphatic and aromatic hydrocarbons, such as benzene, toluene, xylene, cyclohexanone, isophorone, and mineral oil fractions.

Suitable solid vehicles that may be used are mineral earths, such as siliceous clay, silica gel, talc, kaolin, attaclay, limestone, silicic acid, and plant products, such as flour.

Surface-active substances may be named, such as calcium-lignin sulfonate, polyoxyethylene-octyl phenol ether, naphthalene-sulfonic acids, phenolsulfonic acids, formaldehyde condensates, fatty alcohol sulfates and fatty acid alkali and alkaline earth salts.

Surprisingly, it has been found that the herbicidal action and the selectivity of the agents are increased when they contain the surface-active substances in proportions in excess of the usual quantities.

The proportion of the active substance(s) in the various preparations may vary within wide limits. For example, the agents contain about 20 to 80 per cent by weight of active substances, about 80 to 20 per cent by weight of liquid or solid vehicles, and up to 30 per cent by weight of surface-active substances.

The application of the agents may be carried out in the usual manner, such as with water as vehicle in spray solution quantities of 100 to 1000 liter/ha. For total weed control, required spray solution quantities of more than 1000 liters/ha may be applied. The use of the agents in so-called "ultra low volume" is likewise possible, as well as their application in the form of so-called micro-granulates.

The agent may be used in the pre-emergence as well as in the post-emergence stage. For use as weed control in rice cultivation, the agent is expediently applied onto the water surface of the flooded fields.

The compounds to be used according to the invention are known or can be produced by known methods, of which the following should be mentioned.

I. By the reaction of tetraalkyl tin compounds of the general formula

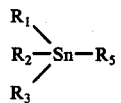  IV with tin halides, trialkyl halides, e.g. tributyl tin chloride, being formed by a coproportionation reaction at elevated temperature.

$R_1$, $R_2$, $R_3$ and $R_5$ here represent identical or different or substituted alkyl radicals.

II. By the reaction of trialkyl tin halides of the general formula

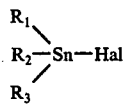  V with alkali hydroxides, preferably in aqueous solution, trialkyl tin oxides or bis-(trialkyl tin) oxides of the formula

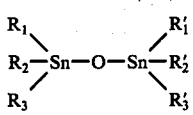  VI being formed.

$R_1$, $R_2$, $R_3$, $R_1'$, $R_2'$, and $R_3'$ here have the above named meaning and Hal represents a halogen atom, such as chlorine.

III. By reaction of trialkyl tin halides of the general formula stated under II with salts of hydrohalic or pseudo hydrohalic acid, e.g. sodium fluoride or potassium thiocyanate, the halogen being substituted by other halogens or pseudo halogens, such as fluorine or by the thiocyanate radical.

As halogen and pseudo hydrohalogen compounds, examples are hydrofluoric, hydrochloric, hydrobromic, hydroiodic, hydrocyanic, or thiocyanic acid as well as cyanic acid.

IV. By reaction of the trialkyl tin or bis-(trialkyl tin) oxides of the general formula stated under II. with oxygen-, sulfur-, or nitrogen-acid compounds, compounds of the general formula

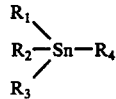  VII being obtained.

The radicals $R_1$, $R_2$, $R_3$ have therein the above named meaning, and $R_4$ represents the radical of the oxygen, sulfur, or nitrogen-acid compounds used in the reaction.

By oxygen-, sulfur-, or nitrogen-acid compounds must be understood those compounds which upon elimination of a hydrogen atom result in the above described radical $R_4$, such as benzoic acids, sulfosalicylic acids, phenols, carboxylic acids, boric acids, hydroxyquinolines, imidazoles, toluylic acid, and others.

As carboxylic acids there may be used stearic acid, maleic acid, oleic acid, or synthetic carboxylic acids which are obtained by carboxylation of branched olefins. This includes such compounds as 2,2,4,4-tetramethyl-valerianic acid, 2-isopropyl-2,3-dimethylbutyric acid or mixtures thereof, the reaction products of which are designated below as VERSATATES.

The following examples will explain the production of the compounds to be used according to the invention.

1. Tri-n-Butyl Tin Chloride 250 g of tetra-n-butyl tin are heated with 62.5 g of stannic tetrachloride with agitation for 3 hours at 210° C.

After cooling, the product is filtered. One obtains 298 g of tri-n-butyl tin chloride.

Tin content: 36.4% (theoretical value 36.5%)
Chlorine content: 10.8% (theoretical value 10.9%)

2. Bis-(tri-n-butyl tin) Oxide

To 700 g tri-n-butyl tin chloride and 650 ml dibutyl ether are added under vigorous agitation 104 g sodium hydroxide dissolved in 400 g water.

The mixture is then heated for another 2 hours at about 60° C. After the reaction product has cooled, the aqueous phase is separated. From the organic layer, the dibutyl ether is distilled under vacuum and the residue is filtered from small amounts of a white precipitate.

There is obtained 596 g bis-(tri-n-butyl tin) oxide.
Tin content: 39.9% (theoretical value 39.8%).

3. Tri-n-Butyl Tin Benzoate 250 g bis-(tri-n-butyl tin) oxide are heated with 102 g benzoic acid and 500 ml benzene with reflux and cycling out of the reaction water. The reaction is terminated after about 2 hours. Then the solvent is distilled under vacuum and the residue is filtered at about 30° C.

One obtains 331 g tri-n-butyl tin benzoate with a tin content of 28.6% (theoretical value 28.8%).

In an analogous manner, the following compounds can be produced:

| Compound No. | Name of Compound | Physical Constant |
|---|---|---|
| 1 | Tri-n-butyl tin fluoride | M.p.257° C |
| 2 | Bis-(tri-n-butyl tin) oxide | B.p.174° C/0.9 Torr |
| 3 | Bis-(tri-n-butyl tin) sulfide | B.p.207–210° C/0.7 Torr |
| 4 | Tri-n-butyl tin rhodanide | Oil |
| 5 | Bis-(tri-n-propyl tin) oxide | B.p.142-144° C/1 Torr |
| 6 | Bis-(tri-n-butyl tin) maleinate | M.p.114° C |
| 7 | Tri-n-butyl tin-9-versatate | Oil |
| 8 | Tri-n-butyl tin-3,5-xylenolate | Oil |
| 9 | Tri-n-propyl tin-9-versatate | B.p.186° C/0.1 Torr |
| 10 | Tri-n-butyl tin chloride | B.p.126° C/2 Torr |
| 11 | Tri-n-butyl tin benzoate | M.p. 22° C |
| 12 | 4-Tri-n-butyl tin-4-sulfo-salicylate | M.p.290° C |
| 13 | Tri-n-octyl tin chloride | B.p.172° C/0.05 Torr |
| 14 | Triethyl tin chloride | M.p.15° C |
| 15 | Tri-n-butyl tin pentachloro-phenolate | Oil |
| 16 | Tri-n-butyl tin phenolate | B.p.137° C/0.08 Torr |
| 17 | Tri-n-butyl tin stearate | Oil |
| 18 | Tri-n-butyl tin-4-toluylate | Oil |

-continued

| Compound No. | Name of Compound | Physical Constant |
|---|---|---|
| 19 | Tri-isobutyl tin chloride | M.p. 26° C |
| 20 | Trimethyl tin chloride | M.p. 42° C |
| 21 | Tri-n-butyl tin imidazole | M.p. 62° C |
| 22 | Tri-n-propyl tin imidazole | M.p.130° C |
| 23 | Tri-n-butyl tin borate | Oil |
| 24 | Tribenzyl tin chloride | M.p.128° C |
| 25 | Tri-n-butyl tin-8-hydroxyquinolate | Oil |
| 26 | Tri-isobutyl tin oxide | B.p.140° C/0.01 Torr |

These compounds are soluble in or miscible in or with petroleum ether, acetone and ethanol.

The following examples will illustrate the invention.

EXAMPLE 1

In a greenhouse, millet (Echinochloa c.g.) and water rice were seeded in soil and after development of the first to second leaf stage, immersed in water 6 cm deep, so that the millet and rice plants were completely under water.

The treatment was then carried out by spraying the agents onto the water surface in a quantity of 1 kg of active substance per hectare for the agent of the invention and 4 kg active substance per hectare for the known comparison agent molinate. The agents were here applied as emulsions in 500 liters of water per hectare. After two weeks, the evaluation was then made by scoring according to the rating scale of 0 = totally destroyed to 10 = not damaged.

The test findings show both a better weed action and an excellent algicidal action of the agents according to the invention in comparison with the known agent which, despite the four times higher quantity used, exhibits an unsatisfactory herbicidal action and is completely inactive against algae.

| Agent of Invention | Kg active substance per hectare | Rice | Millet | Algae growth |
|---|---|---|---|---|
| Compound # | | | | |
| 1 | 1 | 10 | 0 | 0 |
| 2 | 1 | 10 | 0 | 0 |
| 3 | 1 | 10 | 0 | 0 |
| 4 | 1 | 10 | 0 | 0 |
| 5 | 1 | 10 | 0 | 0 |
| 6 | 1 | 10 | 0 | 0 |
| 7 | 1 | 10 | 0 | 0 |
| 8 | 1 | 10 | 0 | 0 |
| 9 | 1 | 10 | 0 | 0 |
| 10 | 1 | 10 | 0 | 0 |
| 11 | 1 | 10 | 0 | 0 |
| 12 | 1 | 10 | 0 | 0 |
| 13 | 1 | 10 | 0 | 0 |
| 14 | 1 | 10 | 0 | 0 |
| 15 | 1 | 10 | 0 | 0 |
| 16 | 1 | 10 | 0 | 0 |
| 17 | 1 | 10 | 0 | 0 |
| 18 | 1 | 10 | 0 | 0 |
| 19 | 1 | 10 | 0 | 0 |
| 20 | 1 | 10 | 0 | 0 |
| 21 | 1 | 10 | 0 | 0 |
| 22 | 1 | 10 | 0 | 0 |
| 23 | 1 | 10 | 0 | 0 |
| 24 | 1 | 10 | 0 | 0 |
| 25 | 1 | 10 | 0 | 0 |
| Comparison Agent | | | | |
| Molinate | 4 | 10 | 4 | 10 |
| Untreated Control | — | 10 | 10 | 10 |

EXAMPLE 2

In a greenhouse, the agents to be used according to the invention were sprayed onto the plants listed below. The treatment occurred in post-emergence in a quantity of 3 kg active substance per hectare, the agents being applied as emulsions in 500 liters of water per hectare.

The evaluation occurred two weeks after the treatment by scoring according to the rating of: 0 = totally destroyed to 10 = not damaged.

The findings show the excellent tolerance of the agent according to the invention, at very high weed action.

| Agents of Invention | kg active subst. /ha | Peanut | Pea | Corn | Rice | Stellaris media | Senecio Vulgaris | Matricaria chamomilla | Laminum amplixi-caule | Centaurea Cyanus | Amaranthus retroflexus | Galium aparine | Chrysanthemum segetum | Ipomoea purpurea | Polygonum lapathifolium | Echinochloa crus galli | Setaria italica |
|---|---|---|---|---|---|---|---|---|---|---|---|---|---|---|---|---|---|
| Compound #1 | 3 | 8 | 8 | 10 | 10 | 1 | 0 | 1 | 0 | 0 | 0 | 0 | 0 | 1 | 0 | 0 | 2 |
| 3 | 3 | 8 | 9 | — | 10 | 0 | 0 | 1 | 0 | 0 | 0 | 0 | 0 | 0 | 0 | 0 | 2 |
| 5 | 3 | 8 | — | — | 10 | 0 | 0 | 0 | 0 | 0 | 0 | 0 | 0 | 5 | 0 | 0 | 0 |
| 9 | 3 | — | 8 | — | 10 | 0 | 0 | 0 | 0 | 0 | 0 | 0 | 0 | 0 | 0 | 0 | 1 |
| 6 | 3 | — | — | 9 | 10 | 2 | 0 | 1 | 0 | 0 | 0 | 0 | 0 | 0 | 0 | 0 | 1 |
| 2 | 3 | — | — | — | 10 | 0 | 0 | 2 | 0 | 0 | 0 | 0 | 0 | 0 | 0 | 0 | 1 |
| 4 | 3 | — | — | — | 10 | 1 | 0 | 1 | 0 | 0 | 0 | 0 | 0 | 0 | 0 | 0 | 1 |
| 7 | 3 | — | — | — | 10 | 1 | 0 | 2 | 0 | 0 | 0 | 0 | 0 | 0 | 0 | 0 | 0 |
| 8 | 3 | — | — | — | 10 | 0 | 0 | 1 | 0 | 0 | 0 | 0 | 0 | 0 | 0 | 0 | 1 |
| 10 | 3 | — | — | — | 10 | 0 | 0 | 0 | 0 | 0 | 0 | 1 | 0 | 0 | 0 | 0 | 0 |
| 11 | 3 | — | — | — | 10 | 0 | 0 | 0 | 0 | 0 | 0 | 1 | 0 | 0 | 0 | 0 | 0 |
| 12 | 3 | — | — | — | 10 | 1 | 0 | 0 | 0 | 0 | 0 | 1 | 0 | 0 | 0 | 0 | 0 |
| 14 | 3 | — | — | — | 10 | 0 | 0 | 0 | 0 | 0 | 0 | 1 | 0 | 0 | 0 | 0 | 0 |
| 15 | 3 | — | — | — | 10 | 0 | 0 | 0 | 0 | 0 | 0 | 1 | 0 | 0 | 0 | 0 | 0 |
| 16 | 3 | — | — | — | 9 | 0 | 0 | 0 | 0 | 0 | 0 | 0 | 1 | 0 | 0 | 0 | 0 |
| 17 | 3 | — | — | — | 10 | 0 | 0 | 0 | 0 | 0 | 0 | 0 | 0 | 0 | 0 | 0 | 0 |
| 18 | 3 | — | — | — | 10 | 0 | 0 | 0 | 0 | 0 | 0 | 1 | 0 | 0 | 0 | 0 | 0 |
| 19 | 3 | — | — | — | 10 | 0 | 0 | 0 | 0 | 0 | 0 | 1 | 0 | 0 | 0 | 0 | 0 |
| 20 | 3 | — | — | — | 9 | 0 | 0 | 0 | 0 | 0 | 0 | 0 | 0 | 0 | 0 | 0 | 0 |

-continued

| Agents of Invention | kg active subst. /ha | Pea-nut | Pea | Corn | Rice | Stel-lar-is med-ia | Se-ne-cio Vul-gar-is | Matri-caria chamo-milla | La-mi-um am-plix-i-caule | Cen-taur-ea Cy-an-us | Amar-anthus retro-flexus | Gal-ium ap-ar-ine | Chrys-anthe-mum sege-tum | Ipo-moea pur-pur-ea | Poly-gonum lapa-thi-folium | Echi-no-chloa crus galli | Se taria ital-ica |
|---|---|---|---|---|---|---|---|---|---|---|---|---|---|---|---|---|---|
| 21 | 3 | — | — | — | 10 | 0 | 0 | 0 | 0 | 0 | 0 | 1 | 0 | 0 | 0 | 0 | 0 |
| 22 | 3 | — | — | 9 | 10 | 0 | 0 | 0 | 0 | 0 | 0 | 0 | 0 | 0 | 0 | 0 | 0 |
| 23 | 3 | — | — | — | 10 | 0 | 0 | 0 | 0 | 0 | 0 | 0 | 0 | 0 | 0 | 0 | 0 |
| 24 | 3 | 9 | 9 | 10 | 10 | — | 5 | 5 | — | — | 1 | — | — | 4 | 2 | — | 5 |
| 25 | 3 | — | — | — | 10 | 0 | 0 | 0 | 0 | 0 | 0 | 1 | 0 | 0 | 0 | 0 | 1 |
| 26 | 3 | — | — | — | 10 | 0 | 0 | 0 | 0 | 0 | 0 | 1 | 0 | 0 | 0 | 0 | 0 |
| Untreated control | — | 10 | 10 | 10 | 10 | 10 | 10 | 10 | 10 | 10 | 10 | 10 | 10 | 10 | 10 | 10 | 10 |

EXAMPLE 3

The plants listed in the following table were treated with the agents to be used according to the invention and with the comparison agent molinate before emergence. The quantity used was 3 kg active substance/ha. The evaluation was made 3 weeks after the treatment by scoring (0 = total destruction; 10 = no damage).

As is evident from the result, the agent used according to the invention excels by a high compatibility with the crop plants and by intensive control of the weed plants. The comparison agent damaged the weed plants insufficiently.

| Agents of Inven- tion | kg ac- tive subst. /ha | Cu- cum- ber | Bush bean | Cot- ton | Pea- nut | Soy- bean | Corn | Wheat | Bar- ley | Oats | Stel- lar- ia med- ia | Sen- ecio vul- gar- is | Ma- tri- car- ia cha- mo- mil- la | La- mi- um am- plex- i- caule | Cen- taur- ea cy- an- us | A- mar- an- thus re- tro- flex- us | Chr- ys- an- the- mum sege- tum | Po- ly- go- nym la- pa- thi- fol- ium | Poa anua |
|---|---|---|---|---|---|---|---|---|---|---|---|---|---|---|---|---|---|---|---|
| Compound #1 | 3 | — | 10 | 10 | 10 | 10 | 10 | — | — | — | 1 | 1 | 0 | 2 | 1 | 0 | 1 | 0 | 0 |
| 2 | 3 | 10 | 10 | 10 | 10 | 10 | 8 | — | — | 8 | 1 | 1 | 0 | 2 | 0 | 0 | 2 | 1 | 0 |
| 3 | 3 | 10 | 10 | 10 | 10 | 10 | 10 | 10 | 10 | 10 | 2 | 1 | 0 | 2 | 0 | 0 | 2 | 2 | 1 |
| 4 | 3 | 10 | 10 | 10 | 10 | 10 | 8 | — | 10 | 10 | 2 | 3 | 0 | 2 | 2 | 0 | 0 | 1 | 1 |
| 5 | 3 | — | — | — | 10 | — | — | — | — | — | 0 | 0 | 0 | 0 | 0 | 0 | 0 | 0 | 0 |
| 6 | 3 | — | 10 | 10 | 10 | 10 | 8 | 8 | 10 | 10 | 1 | — | 0 | — | 1 | 0 | 2 | 1 | 0 |
| 7 | 3 | 10 | — | — | 10 | 10 | 8 | 10 | 10 | 10 | 2 | 0 | 0 | — | 1 | 0 | 1 | 2 | 0 |
| 8 | 3 | 10 | — | 10 | 10 | 10 | 10 | 10 | 10 | 10 | 1 | 1 | 0 | — | 1 | 0 | — | 2 | 0 |
| 9 | 3 | — | — | 8 | 10 | — | 8 | — | — | — | 1 | 0 | 0 | 0 | 0 | 0 | 0 | 1 | 0 |
| 10 | 3 | 8 | 9 | 10 | 10 | — | 9 | — | — | — | 0 | — | 0 | 0 | 0 | 0 | 0 | 0 | 0 |
| 11 | 3 | — | 9 | 10 | 10 | — | 9 | — | — | — | 0 | — | 0 | 0 | 0 | 0 | 0 | 0 | 0 |
| 12 | 3 | 9 | 10 | — | 10 | — | 10 | 8 | — | — | 0 | — | 0 | 0 | 1 | 0 | 2 | 0 | 1 |
| 15 | 3 | — | 10 | — | 10 | — | 9 | — | — | — | 0 | — | 0 | 1 | 1 | 0 | 0 | 1 | 1 |
| 16 | 3 | — | 10 | 10 | 8 | — | 10 | — | — | — | 0 | — | 0 | 1 | 0 | 0 | 0 | 0 | 1 |
| 17 | 3 | — | — | 10 | 9 | — | 10 | — | — | — | 0 | — | 0 | 1 | 0 | 0 | 1 | 0 | 1 |
| 18 | 3 | — | — | 8 | 8 | — | — | — | — | — | 0 | — | 0 | 0 | 0 | 0 | 0 | 0 | 0 |
| 20 | 3 | — | 9 | 8 | 10 | — | 9 | — | — | — | 0 | — | 0 | 1 | 0 | 0 | 0 | 0 | 0 |
| 21 | 3 | — | — | 9 | 10 | — | 9 | — | — | — | 0 | — | 0 | 0 | 0 | 0 | 0 | 0 | 0 |
| 22 | 3 | — | 10 | 8 | 9 | — | 10 | — | — | — | 0 | — | 0 | 0 | 0 | 0 | 0 | 0 | 0 |
| 23 | 3 | — | 10 | 8 | 9 | — | 10 | — | — | — | 0 | — | 0 | 0 | 0 | 0 | 0 | 0 | 0 |
| 25 | 3 | — | — | — | 10 | — | 8 | — | — | — | 0 | — | 0 | 0 | 0 | 0 | 0 | 0 | 0 |
| 26 | 3 | — | — | 10 | 8 | 8 | 9 | — | — | — | 0 | — | 0 | 0 | 0 | 0 | 1 | 0 | 0 |
| Com- pari- son Agent Molin- ate | 3 | 10 | 10 | 5 | — | 3 | 10 | 10 | 10 | 5 | 8 | 10 | 6 | 0 | 10 | 5 | 10 | 10 | 10 |

EXAMPLE 4

Rice and Eleocharis in flowerpots were placed in overpots filled with water, so that the plants were completely covered with water.

Then, with the agents in aqueous emulsions, an area spraying was carried out directly onto the water surface. The quantity used was 4 kg of active substance per hectare.

The evaluation occurred 19 days after the treatment by scoring (0 = total destruction, 10 = no damage).

As the results show, the agent according to the invention is clearly superior to the comparison agent in the weed action.

| Agent of Invention | | kg active substance/ha. | Rice | Eleocharis |
|---|---|---|---|---|
| Compound No. | 1 | 4 | 10 | 0 |
| | 2 | 4 | 10 | 0 |
| | 3 | 4 | 10 | 1 |
| | 4 | 4 | 10 | 0 |
| | 5 | 4 | 10 | 0 |
| | 6 | 4 | 10 | 0 |
| | 7 | 4 | 10 | 0 |
| | 8 | 4 | 10 | 0 |
| | 9 | 4 | 10 | 0 |
| | 11 | 4 | 8 | — |
| | 14 | 4 | 8 | — |
| | 16 | 4 | 10 | 0 |
| | 17 | 4 | 9 | 0 |
| | 18 | 4 | 9 | 0 |
| | 21 | 4 | 9 | 0 |
| | 22 | 4 | 10 | 0 |
| | 23 | 4 | 8 | 0 |
| | 26 | 4 | 8 | 0 |
| Comparison agent Molinate | | 4 | 10 | 10 |

We claim:

1. A method for the treatment of rice fields for the control of weed growth which comprises applying to the water surface of flooded rice fields from about 0.5 to about 10 kilograms per hectare of tri-n-butyl tin imidazole.

* * * * *